United States Patent [19]

Tsai et al.

[11] Patent Number: 5,360,575
[45] Date of Patent: Nov. 1, 1994

[54] LACTIC ACID DERIVATIVES HAVING TWO ASYMMETRIC CARBON ATOMS, LIQUID CRYSTAL COMPOSITION CONTAINING SAME AND LIQUID CRYSTAL DEVICE

[75] Inventors: Wen-Liang Tsai, Hsinchu; Hwei-Long Kuo, Taipei, both of Taiwan, Prov. of China

[73] Assignee: Industrial Technology Research Institute, Hsinchu, Taiwan, Prov. of China

[21] Appl. No.: 790,246

[22] Filed: Nov. 8, 1991

[51] Int. Cl.$^5$ .................. C09K 19/52; C09K 19/20; C07C 69/76; G02F 1/13
[52] U.S. Cl. ............ 252/299.01; 252/299.64; 252/299.65; 252/299.66; 252/299.67; 560/59; 560/64; 560/84; 560/87; 560/180; 568/583; 568/659; 359/10
[58] Field of Search ............ 252/299.01, 299.62, 252/299.61, 299.64, 299.65, 299.66, 299.67; 359/103, 104; 560/44, 59, 64, 76, 84, 87, 180; 568/579, 583, 626, 659

[56] References Cited

U.S. PATENT DOCUMENTS

| | | | |
|---|---|---|---|
| 5,080,827 | 1/1992 | Miyazawa et al. | 252/299.66 |
| 5,185,097 | 2/1993 | Toshida et al. | 252/299.01 |

OTHER PUBLICATIONS

R. B. Meyer: Ferroelectric Liquid Crystals; 1975; pp. L-69 to L-71.

Noel A. Clark: Submicrosecond Bistable Electro-Optic Switching in Liquid Crystals; 1980; pp. 899 to 901.
W. Kuczynski: Ferroelectric Properties of Smectic Liquid Crystals with Induced Helical Structure; 1980; pp. 123-126.
Uni. of Pisa: The 14th International Liquid Crystal Conference; 1992; pp. 164, 165, 253, 304.
B. Otterhoom: Synthesis and Electro-Optical Properties of Some Rerroelectric Liquid Crystals Derived from Lactic Acid.
A. M. Lackner: Properties of New Ferroelectric Materials; 1989; 1259 to 1267.

*Primary Examiner*—Shean Wu
*Attorney, Agent, or Firm*—Ladas & Parry

[57] ABSTRACT

An optically active lactic acid derivative having the formula (1a):

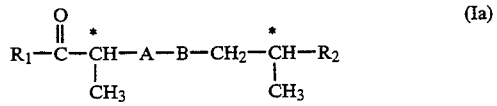

wherein A is O or S; B is —(CH$_2$)$_m$— or —(CH$_2$)$_n$—O; R1 is an alkoxy group having 1-22 carbon atoms, a phenolate, a substituted phenolate, a hydroxy group, or a halogen atom; R2 is an alkyl group having 2-8 carbon atoms; m is 0, 1, 2, 3 or 4; n is 2, 3, 4 or 5; C* is an asymmetric carbon atom. Liquid crystal compositions and liquid crystal devices containing the above mentioned derivatives are also disclosed.

34 Claims, No Drawings

LACTIC ACID DERIVATIVES HAVING TWO ASYMMETRIC CARBON ATOMS, LIQUID CRYSTAL COMPOSITION CONTAINING SAME AND LIQUID CRYSTAL DEVICE

BACKGROUND OF THE INVENTION

Field of the Invention

This invention relates to optically active lactic acid derivatives having two asymmetric centers, liquid crystal compositions containing said optically active lactic acid derivatives and liquid crystal devices thereof.

The technology of liquid crystal displays has been developed rapidly due to the invention of novel nematic liquid crystals, the discovery of their electro-optic effects and the development of their applications in electronic industries such as electronic watch industries and computer display industries. Liquid crystals also have potential use in television displays (HDTV). However, further improvements are desired so as to improve their contrast, view angle and their switching speed.

In 1975, Meyer et. al. found that chiral smectic C phase is ferroelelctric after a series of experiments conducted on p-(decyloxy) benzylidene-amino-2-methylbutyl-cinnamate (R. B. Meyer, L. Liebert, L. Strzelecki and P. Keller, "Ferroelectric Liquid Crystals" J. Physique Lett., 1975, 36, L69). Since then, the development and the application of such smectic phase liquid crystals have become a challenging research field. In 1980, Clark and Lagerwall invented a device employing such liquid crystals, i.e. an SSFLC (surface-stabilized ferroelectric liquid crystal) light valve which is a basic device of new electro-optic technology (N.A. Clark, S.T. Lagerwall, Appl. Phys. Lett., 1980, 36, 899). The unique advantages of ferroelectric liquid crystals in the speed of switching and in optically memorizing characteristics have led such liquid crystals to its importance in flat panel displays.

The ferroelectricity of ferroelectric liquid crystals are mainly contributed by optically active molecular part of the liquid crystals formed by asymmetric synthesis. Ferroelectric liquid crystal displays generally employ a mixture of liquid crystals in which chiral compounds are used as chiral dopant. The chiral dopant may or may not have chiral smectic C phase (W. Kuczynski, H. Stegemeyer, Chem. Phys. Lett., 1980, 70, 123; F. Leenhouts, S. M. Kelly, A. villiger, Displays, 1990, 41). Intrinsically ferroelectric liquid crystal is also one of nonlinear optical materials which are now under intensive study worldwide.

Lactic acid is a commercially available optically active material which consists of easily convertible functional groups, i.e. hydroxy and carboxy groups, which can be easily converted into other molecular structures. In U.S. Pat. Nos. 4,880,560, 4,852,977, 4,812,259 and 4,556,727 discloses optically active lactic acid derivatives and their applications in liquid crystal compositions and devices. The lactic acid derivatives disclosed therein contain only a single asymmetric center. Their performances in displays are still needed to be further improved.

SUMMARY OF THE INVENTION

This invention provides novel optically active lactic acid derivatives having two asymmetric centers and chiral liquid crystal structures. These materials exhibit superior liquid crystal characteristics and are useful for liquid crystal display devices.

It has been believed that the introduction of a second asymmetric center into the chiral molecular composition of a ferroelectric liquid crystal would either narrow the temperature range of a needed liquid crystal phase or damage the formation of the liquid crystal phase. Therefore latic acid derivatives with two asymmetric centers synthesized by the etherification of α-hydroxy group of lactate with a chiral compound are hitherto unknown at the science and technology of liquid crystals. The Applicants unexpectedly found that lactic acid derivatives with two asymmetric centers obtained according to their invention exhibit a smectic A phase, or chiral smectic C and chiral nematic phases, or smectic A and chiral smectic C phase, and that the chiral smectic C phases thereof have broad temperature ranges.

The lactic acid derivatives according to this invention have the general formula:

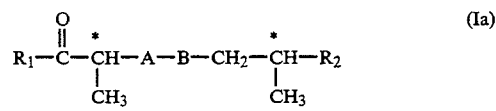

wherein A is O or S; B is —$(CH_2)_m$— or —$(CH_2)_n$—O; R1 is an alkoxy group having 1–22 carbon atoms, a phenolate, a substituted phenolate, a hydroxy group or a halogen; R2 is an alkyl group having 2–8 carbon atoms; m is an integer of 0–4, n is an integer of 2–5, and C* is an asymmetric carbon atom.

Preferred compounds of formula (1a) are those in which R1 is methoxy, ethoxy, propanoxy, butoxy, pentoxy, hexoxy, hydroquinone, 4,4'- biphenol, hydroxy or Cl; A is O; B is —$(CH_2)_m$— where m is 0; and/or R2 is ethyl.

The above-mentioned optically active lactic acid derivatives can be synthesized from lactic acid or thiolactic acid by the esterification of lactic acid or thiolactic acid and then by the etherification of —OH— or —SH— group with chiral alkyl halides or sulfonates. After saponification, esters are converted to the corresponding organic acids which in turn can be converted into respective acid halides.

The organic acids or acid halides obtained as mentioned above can be used to prepare optically active liquid crystal materials by the esterification of the organic acids or acid halides with another hydroxy containing molecules which may or may not have a liquid crystal phase. And the optically active lactic acid derivatives containing hydroquinone or 4,4'-biphenol as mentioned above can also be used to prepare optically active liquid crystal materials by the reaction with another organic acids or acid chlorides which may or may not have a liquid crystal phase, The liquid crystal material according to the present invention has the general formula:

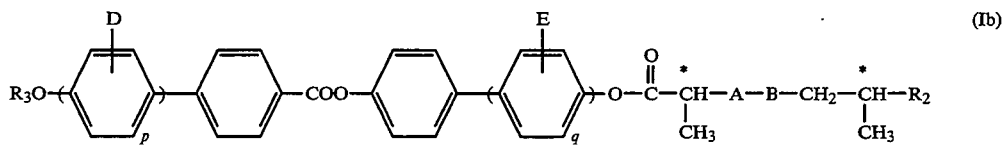

wherein A is O or S; B is —(CH$_2$)$_m$— or —(CH$_2$)$_n$—O; R2 is an alkyl group having 2-8 carbon atoms; m is an integer of 0-4; n is an integer of 2-5; p is 0 or 1; q is 0 or 1; D and E are independently H or a halogen atom or a nitro group; R3 is a linear alkyl group having 1-22 carbon atoms; C* is an asymmetric carbon atom.

Preferred compounds of formula (1b) are those in which R$_3$ is a linear alkyl group having 3-12 carbon atoms; A is O; B is —(CH$_2$)$_m$—, m is 0; D and E are independently hydrogen or fluorine atom; p or q is 1; and/or R2 is ethyl.

Optically active liquid crystal compositions can be prepared from the compounds of formula (1a) and (1b). The compositions may contain at least one compound of formula (1a) or (1b), a mixture of compounds of formula (1a), a mixture of compounds of formula (1b), or a mixture of at least one compound of formula (1a) and at least one compound of formula (1b). The compositions may also be a mixture of at least one compound of formula (1a) or (1b) with another liquid crystal materials.

The lactic acid derivatives according to this invention can be used in liquid crystal devices by filling one of the above mentioned compositions between two substrate plates in a conventional way. The liquid crystal devices according to this invention may be liquid crystal light valves or non-linear optical devices.

Hereinbelow, the present invention will be explained more specifically by way of examples.

EXAMPLE 1

Preparation of a compound of formula (1a) (A is O, B is —(CH$_2$)$_m$—, m is 0, R1 is OC$_2$H$_5$, and R2 is C$_2$H$_5$)

1.18g (10.0 mmol) of (S)-lactic acid ethyl ester, 3.00g (15.2 mmol) of (S)-1-iodo-2-methylbutane, and 4.00g(17.2 mmol) of silver oxide were mixed and stirred in a reaction bottle for 15 hours at 70 deg C. The reaction bottle was cooled to room temperature. The reaction product was extracted with ethyl ether (4×50 ml). The ether extract was washed with 10% KOH solution (2×50 ml) and water (2×50ml). The organic phase was dried over anhydrous magnesium sulfate. Filtration add the removal of solvent by rotary evaporation gave 1.31 g of crude product which was purified by flash chromatography (SiO2, hexane/ethyl acetate 9:1) affording 0.84 gm (45% yield) of colorless product.

$[\alpha]_D^{17} = -50.9°$ (C=1.01, CHCl$_3$). 'H-NMR analysis gave the following data:

'H-NMR analysis gave the following data:

$^1$HNMR:

| δ | 4.16 | 3.88 | 3.40 | 3.05 | 1.64 | 1.36 | 1.25 | 1.13 | 0.85 |
|---|------|------|------|------|------|------|------|------|------|
| H | 2H   | 1H   | 1H   | 1H   | 1H   | 4H   | 3H   | 1H   | 6H   |

EXAMPLE 2

Preparation of a compound of formula (1a) (A is O, B is —(CH$_2$)$_m$—, m is 0, R1 is OH, and R2 is C$_2$H$_5$)

0.84g (4.5 mmol) of the product of Example 1 was dissolved in a solution containing 10ml of 10% KOH solution and 80% ethanol and refluxed for 1 hour. The reaction solution was cooled and stirred in an ice water bath. Concentrated HCl was added dropwise, until the solution became acidic. Ethanol was removed and the product was extracted by ethyl ether (5×50 ml). The ether extract was dried over anhydrous magnesium sulfate. Filtration and removal of solvent by rotary evaporation gave 0.70g (95% yield) of organic acid product. $[\alpha]_D^{17} = -14.6°$ (C=1.02, CHCl$_3$).

'H-NMR analysis gave the following data:

$^1$HNMR:

| δ | 3.93 | 3.43 | 3.15 | 1.62 | 1.41 | 1.13 | 0.86 |
|---|------|------|------|------|------|------|------|
| H | 1H   | 1H   | 1H   | 1H   | 4H   | 1H   | 6H   |

EXAMPLE 3

Preparation of the compound of formula(1b)(A is O, B is —(CH$_2$)$_m$, m is 0, D is hydrogen, p and q are both 0, R2 is C$_2$H$_5$, and R3 is C$_8$H$_{17}$)

4.6 g (200 mmol) of Na was dissolved in 300 ml of ethanol (99%). 13.5 g (98 m mol) of p-hydroxybenzoic acid was added to the solution followed by the addition of 20.3 g (105 mmol) of 1-bromooctane 15 min later. The solution was refluxed for 4 hours. 30 ml of 10% KOH solution was added and the mixture was refluxed for 2 hours, cooled, and acidified with concentrated HCl After filtration, 19.8 g of solid was obtained. Recrystallization of the solid from ethanol gave 17.1 g (69% yield) of pure crystalline substance (I).

2.5 g (10 mmol) of crystalline substance (I) was dissolved in 10 ml of benzene. Then, 15 mmol of oxalyl chloride was added to the above solution within 10 min. The solution was refluxed for 3 hours and excess oxalyl chloride was removed under high vacuum. 5 ml of dichloromethane was added to form solution A.

Solution B was prepared by dissolving 11 mmol of p-(benzyloxy)phenol in 1 ml of pyridine and 10 ml of dichloromethane.

Solution B was gradually added to solution A within 5 min. After stirring for 30 min; the solvents were removed and the solid was recrystallized from ethanol. 3.8 g (88% yield) of crystalline substance (II) was obtained.

2.16 g (5 mmol) of solid substance (II) was mixed with 35 ml of ethanol and 0.9 g of Pd/C (10%). After the hydrogenation was completed, Pd/C was filtered off and the solvent was removed by rotary evaporation. Recrystallization of crude product from hexane and ethyl acetate gave 1.4 g (82% yield) of pure product (III).

0.6 g (3.75 mmol) of the organic acid product obtained in Example 2 was dissolved in 10 ml of benzene. 6 mmol of oxalyl chloride was added within 5 min and then refluxed for 3 hours. After removal of excess oxalyl chloride under high vacuum, 5 ml of dichloromethane was added thereto for use in the next step.

The product (III) was dissolved in 1 ml of pyridine and 10 ml of dichloromethane The acid chloride solution obtained from the organic acid of Example 2 was added to the above solution within 10 min. After the reaction was complete, the solid was filtered off and the solvent was removed by rotary evaporation. Flash chromatography (SiO2, hexane/ethyl acetate 9:1) of crude product gave 1.34g (74% yield) of pure final product. $[\alpha]_D^{23} = -24.6°$ (c=1.01, CHCl3).

'H-NMR analysis gave the following data:

$^1$H-NMR:

| δ/H | 8.1/2H | 7.2/4H | 6.95/4H | 4.17/2H | 4.0/1H | 3.55/2H | 3.25/1H | 1H | 1.9~1.65/3H |
|---|---|---|---|---|---|---|---|---|---|

$^1$H-NMR:

| δ/H | 1.6~1.1/15H | 0.9/9H |
|---|---|---|

EXAMPLE 4

Preparation of a compound of formula (1b) (A is o, B is —(CH2)$_m$, m is 0, D is H, p is 1, q is 0, R is C2H5, R3 is C12H25)

Instead of 1-bromooctane and p-hydroxybenzoic acid, 1-bromododecane and 4-(4'-hydroxyphenyl) benzoic acid were used in this example respectively. The same preparative procedures as in Example 3 were followed. The product was purified by flash chromatography.

$[\alpha]_D^{25} = -27.4°$ (C=1.00 CHCl3). 'H-NMR analysis gave the following data:

'H-NMR analysis gave the following data:

$^1$HNMR:

| δ/H | 8.20/2H | 7.60/4H | 7.20/4H | 7.00/2H | 4.16/1H | 3.99/2H | 3.58/1H | 3.24/1H | 1.9~1.0/26H | 0.93/9H |
|---|---|---|---|---|---|---|---|---|---|---|

EXAMPLE 5

Preparation of a compound of formula (1a) (A is O, B is —(CH2)$_m$—, m is 0, :R1 is

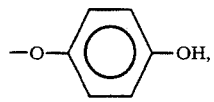

and R2 is C2H5 )

The acid chloride synthesized from the organic acid of Example 2 in the presence of oxalyl chloride was reacted with p-(benzyloxy) phenol. After removal of benzyl group by hydrogenation the crude product was purified by flash chromatography.

$[\alpha]_D^{25} = -36.3°$ (C=1.00 CHCl3)

EXAMPLE 6

Preparation of a compound of formula (1a) (A is O, B is —(CH2)$_m$—, m is 0, R1 is

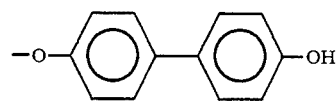

and R2 is C2H5)

The acid chloride synthesized from the organic acid of Example 2 in the presence of oxalyl chloride was reacted with 4,4'-biphenol monobenzyl ether. After removal of benzyl group by hydrogenation the crude product was purified by flash chromatography. 'H-NMR analysis gave the following data:

'H-NMR analysis gave the following data:

'H-NMR:

| δ/H | 7.6-6.8/8H | 5.35/1H | 4.20/1H | 3.60/1H | 3.26/1H | 1.75-1.10/6H |
|---|---|---|---|---|---|---|

| δ/H | 0.98-0.80/6H |
|---|---|

EXAMPLE 7

Table 1 shows examples of optically active liquid crystal materials according to this invention together with their phase transition temperatures.

TABLE 1

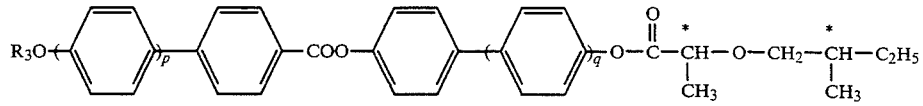

| | | | | Phase & Phase Transition Temperature (°C.) | | | | |
|---|---|---|---|---|---|---|---|---|
| R3 | p | q | * | C | S$_c$* | S$_A$ | N* | I |
| C8H17 | 0 | 0 | S,S | .37 | | (.29) | — | . (Ex.3) |
| C12H25 | 1 | 0 | S,S | .82 | .137 | .149 | — | . (Ex.4) |
| C10H21 | 1 | 0 | S,S | .76 | .139 | .155 | — | . |
| C9H19 | 1 | 0 | S,S | .75 | .140 | .158 | — | . |
| C10H21 | 0 | 1 | S,S | .84 | .128 | — | .133 | . |
| C9H19 | 0 | 1 | S,S | .75 | .120 | — | .127 | . |

C represents solid, S$_c$* represents chiral smectic C phase, S$_A$ represents smectic A phase, N* represents chiral nematic phase, I represents liquid, ( ) represents monotropic liquid crystal phase.

We claim:

1. An optically active lactic acid derivative represented by the following formula:

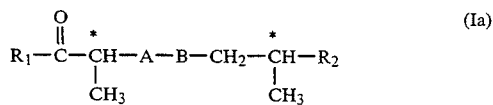

wherein A is O or S; B is —(CH2)$_m$— or —(CH2)$_n$—O: R1 is an alkoxy group having 1-22 carbon atoms, hydroxyphenyloxy, hydroxybiphenyloxy, a hydroxy group, or a halogen atom; R2 is an alkyl group having 2-8 carbon atoms; m is an integer of 0-4, n is an integer of 2-5, and C* is an asymmetric carbon atom.

2. An optically active lactic acid derivative as claimed in claim 2, wherein R1 is methoxy, ethoxy, propanoxy, butoxy, pentoxy, hexoxy, 4-hydroxyphenyloxy, 4,4'hydroxybiphenyloxy, hydroxy or chlorine atom.

3. An optically active lactic acid derivative represented by the following formula:

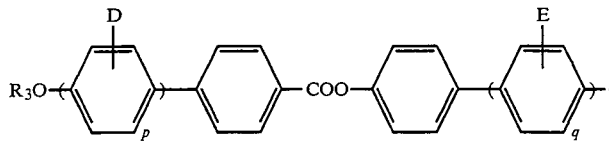

wherein A is O or S, B is —(CH₂)$_m$ or —(CH₂)$_n$—O; R₂ is an alkyl group having 2–8 carbon atoms, m is an integer of 0–4, n is an integer of 2–5, p is 0 or 1, q is 0 or 1; D and E are independently H, a halogen atom or a nitro group;; R₃ is a linear alkyl group having 1–22 carbon atoms; and C* is an asymmetric carbon atom.

4. An optically active lactic acid derivative as claimed in claim 3, wherein R3 is a linear alkyl group having 3–12 carbon atoms.

5. An optically active lactic acid derivative as claimed in claim 1, wherein A is an oxygen atom.

6. An optically active lactic acid derivative as claimed in claim 1, wherein B is —(CH₂)$_m$—, and m is 0.

7. An optically active lactic acid derivative as claimed in claim 3, wherein D and E are independently hydrogen or a fluorine atom.

8. An optically active lactic acid derivative as claimed in claim 1, wherein R2 is ethyl.

9. An optically active lactic acid derivative as claimed in claim 2, wherein A is an oxygen atom, B is —(CH₂)$_m$—, m is 0, and R₂ is ethyl.

10. An optically active lactic acid derivative as claimed in claim 1, which is represented by the formula

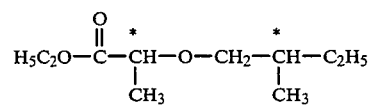

wherein C* represents an asymmetric carbon atom.

11. An optically active lactic acid derivative as claimed in claim 1, which is represented by the formula:

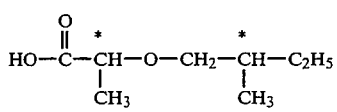

wherein C* represents an asymmetric carbon atom.

12. An optically active lactic acid derivative as claimed in claim 1, which is represented by the formula:

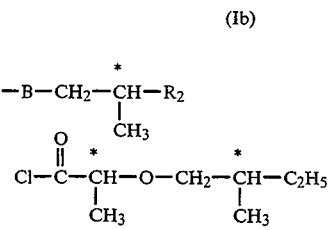

wherein C* represents an asymmetric carbon atom.

13. An optically active lactic acid derivative which is represented by the formula

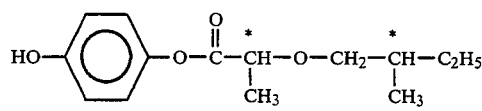

wherein C* represents an asymmetric carbon atom.

14. An optically active lactic acid derivative which is represented by the formula:

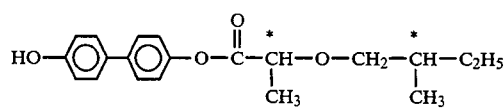

wherein C* represents an asymmetric carbon atom.

15. An optically active lactic acid derivative as claimed in claim 3, which is represented by the formula:

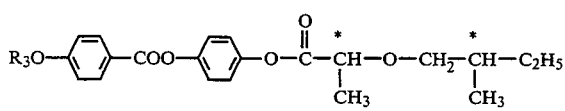

wherein R3 is a linear alkyl group having 1–22 carbon atoms and C* represents an asymmetric carbon atom.

16. An optically active lactic acid derivative as claimed in claim 3, which is represented by the formula:

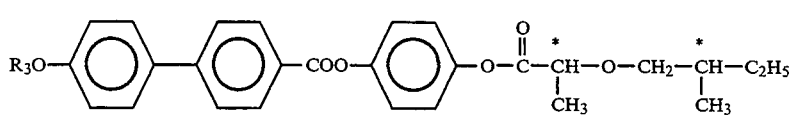

wherein R3 is a linear alkyl group having 1–22 carbon atoms, and C* is an asymmetric carbon atom.

17. An optically active lactic acid derivative as claimed in claim 3, which is represented by the formula:

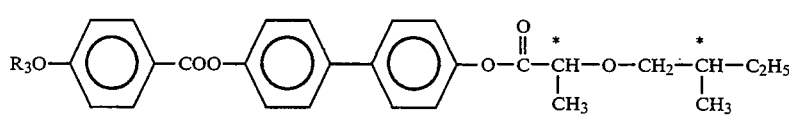

wherein R3 is a linear alkyl group having 1–22 carbon atoms, and C* is an asymmetric carbon atom.

18. A liquid crystal composition comprising at least one optically active lactic acid derivative having the formula:

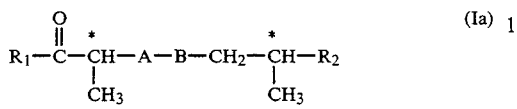

wherein A is O or S; B is —(CH$_2$)$_m$— or —(CH$_2$)$_n$—O; R$_1$ is an alkoxy group having 1–22 carbon atoms, hydroxyphenyloxy, hydroxybiphenyloxy, or a hydroxy group; R$_2$ is an alkyl group having 2–8 carbon atoms; m is an integer of 0–4, n is an integer of 2–5, and C* is an asymmetric carbon atom.

19. A liquid crystal composition as claimed in claim 18, wherein said optically active lactic acid derivative has the formula:

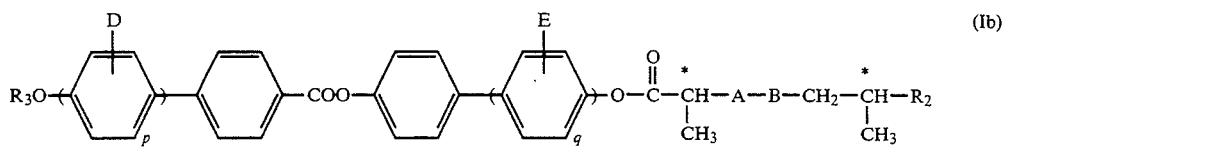

wherein A is O or S, R2 is an alkyl group having 2–8 carbon atoms, m is an integer of 0–4, n is an integer of 2–5, p is 0 or 1, q is 0 or 1; D and E are independently H, or a halogen atom; R3 is a linear alkyl group having 1–22 carbon atoms; and C* is an asymmetric carbon atom.

20. A liquid crystal device containing a pair of substrate plates and a liquid crystal composition filled between the substrate plates, said liquid crystal composition comprising at least one lactic acid derivative having the formula:

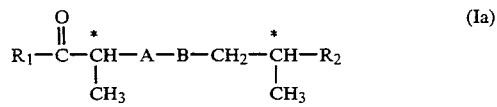

wherein A is O or S; B is —(CH$_2$)$_m$— or —(CH$_2$)$_n$—O; R$_1$ is an alkoxy group having 1–22 carbon atoms, hydroxyphenyloxy, hydroxybiphenyloxy, or a hydroxy group; R$_2$ is an alkyl group having 2–8 carbon atoms; m is an integer of 0–4, n is an integer of 2–5, and C* is an asymmetric carbon atom.

21. A liquid crystal device as claimed in claim 20, wherein said lactic acid derivative has the formula:

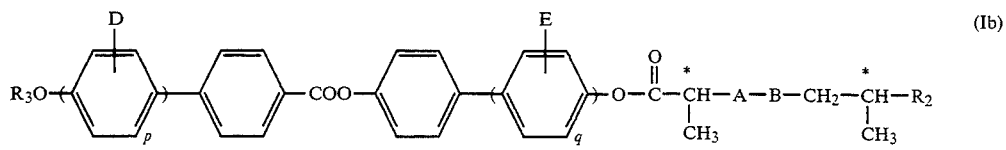

wherein A is O or S, R2 is an alkyl group having 2–8 carbon atoms, m is an integer of 0–4, n is an integer of 2–5, p is 0 or 1, q is 0 or 1; D and E are independently H, a halogen atom or a nitro group; R3 is a linear alkyl group having 1–22 carbon atoms; and C* is an asymmetric carbon atom.

22. An optically active lactic acid derivative as claimed in claim 2, wherein A is an oxygen atom.

23. An optically active lactic acid derivative as claimed in claim 3, wherein A is an oxygen atom.

24. An optically active lactic acid derivative as claimed in claim 4, wherein A is an oxygen atom.

25. An optically active lactic acid derivative as claimed in claim 2, wherein B is —(CH$_2$)$_m$—, and m is 0.

26. An optically active lactic acid derivative as claimed in claim 3, wherein B is —(CH$_2$)$_m$—, and m is 0.

27. An optically active lactic acid derivative as claimed in claim 4, wherein B is —(CH$_2$)$_m$—, and m is 0.

28. An optically active lactic acid derivative as claimed in claim 4, wherein D and E are independently hydrogen or a fluorine atom.

29. An optically active lactic acid derivative as claimed in claim 2, wherein R2 is ethyl.

30. An optically active lactic acid derivative as claimed in claim 3, wherein R2 is ethyl.

31. An optically active lactic acid derivative as claimed in claim 4, wherein R2 is ethyl.

32. An optically active lactic acid derivative as claimed in claim 2, wherein A is an oxygen atom, B is —(CH$_2$)$_m$—, m is 0, and R$_2$ is ethyl.

33. An optically active lactic acid derivative as claimed in claim 3, wherein A is an oxygen atom, B is —(CH$_2$)$_m$—, m is 0, and R$_2$ is ethyl.

34. An optically active lactic acid derivative as claimed in claim 4, wherein A is an oxygen atom, B is —(CH$_2$)$_m$—, m is 0, and R$_2$ is ethyl.

* * * * *